Figure 1:
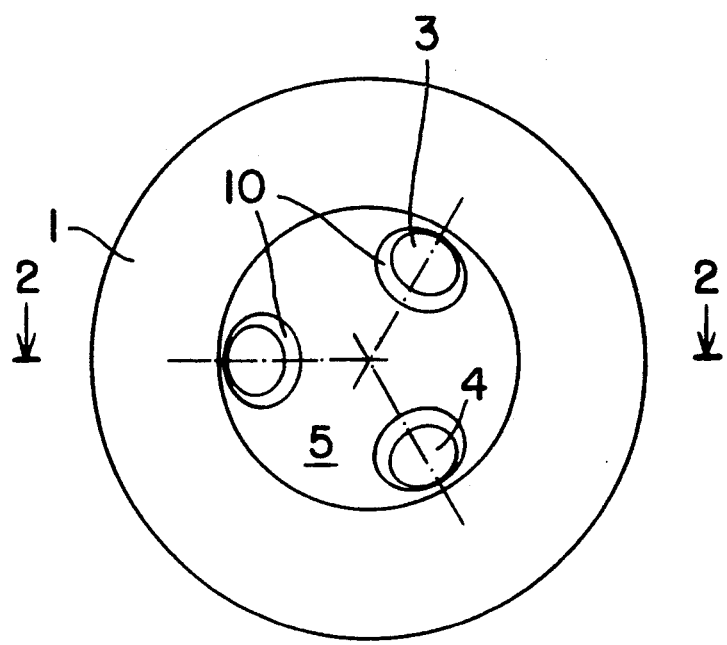

United States Patent [19]

Koch et al.

[11] Patent Number: 5,181,926
[45] Date of Patent: Jan. 26, 1993

[54] BONE IMPLANT HAVING RELATIVELY SLIDABLE MEMBERS

[75] Inventors: Rudolf Koch, Frauenfeld; Robert M. Streicher, Winterthur, both of Switzerland

[73] Assignee: Sulzer Brothers Limited, Winterthur, Switzerland

[21] Appl. No.: 820,358

[22] Filed: Jan. 14, 1992

[30] Foreign Application Priority Data

Jan. 18, 1991 [CH] Switzerland .................. 00145/91

[51] Int. Cl.⁵ .................................................. A61F 2/32
[52] U.S. Cl. .......................................... 623/22; 623/18
[58] Field of Search .......................... 623/18, 22, 23

[56] References Cited

FOREIGN PATENT DOCUMENTS 1189325 4/1970 United Kingdom ............... 623/22
1527498 10/1978 United Kingdom .

*Primary Examiner*—Randy C. Shay
*Attorney, Agent, or Firm*—Kenyon & Kenyon

[57] ABSTRACT

The implant is made of two members which are relatively movable relative to each other. One member is made of hard material while the second member is made of a soft material. In addition, a plurality of support members of hard material are embedded in the soft member and each has a sliding surface to receive the hard member thereon in bearing relation.

5 Claims, 1 Drawing Sheet

BONE IMPLANT HAVING RELATIVELY SLIDABLE MEMBERS

This invention relates to a bone implant having relatively slidable members.

As is known, joint implants, for example, artificial hip or knee joints, are generally constructed with members which are slidable relative to each other. For example, one slide member is frequently made from a relatively soft material, preferably a plastic or a fiber-reinforced plastic so that use can be particularly made of the shock-absorbing and elastic properties of the plastic whereas the other implant member is made from a material which is relatively hard when compared with the first material, for example, a metal or bioceramic. If necessary, the harder member may also be provided with a support of rigid material. A preferred material for the soft slide member is polyethylene, for example, which in certain circumstances may be reinforced with carbon fibers.

Swiss Patent 449,173 describes a metallic cotyloid cavity for an artificial hip joint in which a plurality of slide members of plastic are distributed in the sliding surface. When loaded, these slide members are compressed as elastically resilient elements and open a gap between the sliding surfaces of the hip joint when the load is removed. However, in practice, it has been shown that the soft slide members are subject to an impermissibly high level of abrasion during the course of time and that abraded particles may move into the surrounding living tissue about the artificial joint thereby resulting in undesirable inclusions and, consequently, disturbance and damage.

British Patent 1,527,498 describes a hip joint prosthesis which employs a plurality of insert members of wear-resistent material embedded in a socket which receives a ball member. The insert members are distributed over the hemispherical surface of the socket in such a manner that they are spaced from one another and form a discontinuous hemispherical surface on which the surface of the ball member slidably abuts.

British Patent 1,189,325 describes a hip joint which uses circular discs of synthetic plastic material within a socket for supporting a spherical head thereon.

German OS 2933 174 describes bone implants which can be provided with a multiplicity of pads or the like to form sliding surfaces.

Accordingly, it is an object of the invention to reduce or substantially avoid abrasion of a soft member of two relatively movable members of a bone implant.

Briefly, the invention provides a bone implant which is comprised of a first member of relatively hard material having a bearing surface thereon, a second member of relatively soft material relative to the first member having a bearing surface slidably engaging the bearing surface of the first member and a plurality of support members distributed and embedded in the bearing surface of the second member. Each support member also has a sliding surface made of a hard material relative to the second member and shaped to the bearing surface of the first member.

The hard support members act as low-abrasion or practically abrasion-free slide bearing surfaces when the joint employing the bone implant is subjected to a load. Further, the hard support members are distributed in the bearing surface of the member which is made of soft material, for example, similar to the sliding members of a metal cotyloid cavity. So that the greatest possible "loading surface" is achieved on the support members, the bearing surfaces of the support members are adapted to the bearing surfaces of the hard member of the implant, that is, are constructed as segments of the negative shape of these bearing surfaces.

The contact surfaces with which the support members are supported in the soft implant member and/or the bearing surfaces of the soft member for the support members are dished so as to facilitate the "adjustment" or "adaptation" of the support members to the bearing surfaces of the hard member. With support members dished in this way or soft bearing members, it is advantageous if the peripheral surfaces of the support members and the circumferential walls of the depressions in the to each other and are constructed as segments of spherical surfaces. This insures a certain control over the movement of each support member in the soft bearing member.

Further, the support members may be made of the same material class as the hard member of the bone implant, for example being made of ceramics in the case of a ceramic member and being made of metal in the case of a metal bearing member. It is also possible to manufacture these support members from the same material as the hard bearing member.

Figure 2:
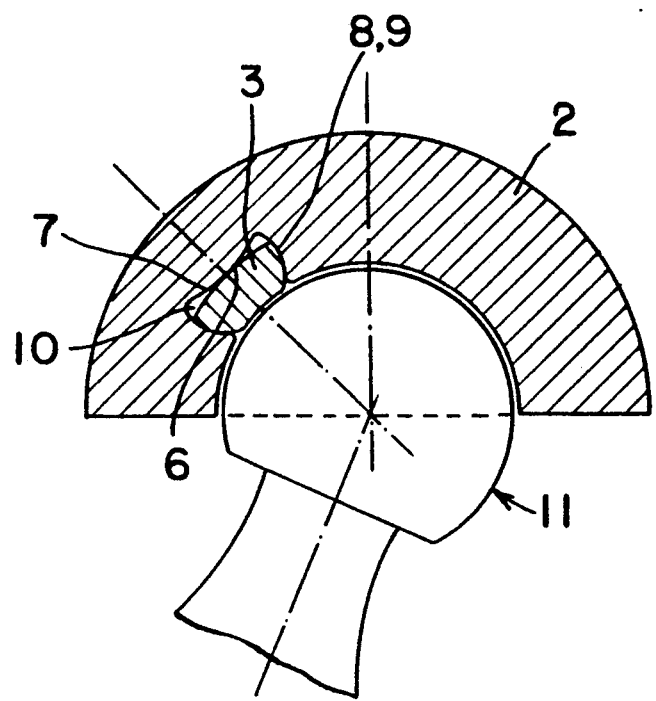

These and other objects and advantages of the invention will become more apparent from the following detailed description taken in conjunction with the accompanying drawings wherein FIG. 1 illustrates a plan view of an acetabular cavity of a bone implant constructed in accordance with the invention; and FIG. 2 illustrates a view taken on line II—II of FIG. 1.

Referring to FIGS. 1 and 2, a bone implant, for example for a hip joint prosthesis includes an artificial acetabulum 1 which is made of relatively soft material, for example, polyethylene, to form one bearing member to cooperate with a condyle of a femur head prosthesis 11 which is manufactured from a hard material, for example, a bioceramic to form a second bearing member. As shown, the acetabulum 1 has a plurality of support members 3 distributed and embedded in depressions 10 within a cotyloid cavity 2. As indicated, the support members 3 are distributed over a spherical bearing surface 5 of the acetabulum 1. Each support member 3 advantageously belongs to the same material class as the femur head prosthesis 11 or at least has a sliding surface 4 made of the same material as the femur head prosthesis 11. In the present example, the femur head prosthesis 11 may be made of a bioceramic material. Hence, the support members 3 are also made of a bioceramic material.

The sliding surface 4 of each support member 3 is integrated as exactly as possible in the sliding surface 5 of the cotyloid cavity 2 and is adapted with respect to its shape, i.e. its radius, to the radius of the cotyloid cavity 2 so as to firstly attain the largest possible "bearing surface" on a support member 3 and secondly to guarantee that the femur head prosthesis 11 slides unimpeded and abrasion-free in the cotyloid cavity 2.

As indicated in FIG. 2, each depression 10 for receiving a support member 3 has a dished surface 7 supporting the support member 3 thereon. Likewise, each support member 3 has a dished surface 6 contacting the dished surface 7 of the respective depression 10. In addition, each support member 3 has a peripheral surface of part-spherical shape while each depression has a circumferential wall of part-spherical shape. Consequently, the relative movements of the support members 3 in the acetabulum 1 are facilitated so that the sliding surfaces 4 of the support members 3 always abut the femur head prosthesis 11 with the largest possible surface.

The invention thus provides a relatively simple structure to avoid abrasion and wear in a bone implant having relatively movable members.

What is claimed is:

1. A bone implant comprising
   a first member of a first material having a bearing surface thereon;
   a second member of a second material, said second material being softer than said first material, said second member having a bearing surface slidably engaging said bearing surface of said first member;
   a plurality of support members distributed and embedded in said bearing surface of said second member, each support member having a sliding surface being made of a hard material relative to said second material and shaped to said bearing surface of said first member; and
   a plurality of depressions in said second member, each depression having a respective support member therein and having a convex surface supporting said respective support member thereon, each support member having a convex surface contacting said convex surface of a respective depression and, wherein each support member has a peripheral surface of part-spherical shape and each depression has a circumferential wall of part-spherical shape.

2. A bone implant as set forth in claim 1 wherein each support member has a peripheral surface of part-spherical shape and each depression has a circumferential wall of part-spherical shape.

3. A bone implant as set forth in claim 2 wherein each support member is made of a material of the same material class as said first member.

4. A bone implant as set forth in claim 1 wherein each support member is made of the same material as said first member.

5. A bone implant as set forth in claim 1 wherein said first member is made of a material selected from the group consisting of metal and bioceramics and said second member is made of a material selected from the group consisting of plastic and fiber-reinforced plastic.

* * * * *

UNITED STATES PATENT AND TRADEMARK OFFICE
CERTIFICATE OF CORRECTION

PATENT NO. : 5,181,926
DATED : January 26, 1993
INVENTOR(S) : Koch et al.

It is certified that error appears in the above-indentified patent and that said Letters Patent is hereby corrected as shown below:

Column 1, line 37, change "resistent" to --resistant--.

Column 2, line 16, after "the" insert --soft member which receive the support members are complementary--;

line 30, change "wherein" to --wherein:--.

Column 4, line 14, change "2" to --1--.

Signed and Sealed this

Seventh Day of June, 1994

Attest:

BRUCE LEHMAN

Attesting Officer     Commissioner of Patents and Trademarks